United States Patent [19]

Hwang et al.

[11] Patent Number: 5,591,883
[45] Date of Patent: Jan. 7, 1997

[54] PROCESS FOR PREPARING CARBONATE COMPOUNDS

[75] Inventors: Kuen-Yuan Hwang; Yu Z. Chen; Chio C. Chu; Hsiao T. Liao, all of Shin-Chu, Taiwan

[73] Assignee: Chang Chun Plastics Co. Ltd., Taipei, Taiwan

[21] Appl. No.: 333,089

[22] Filed: Oct. 31, 1994

[51] Int. Cl.$^6$ .................................................. C07C 69/96
[52] U.S. Cl. ............................ 558/270; 558/275; 558/277
[58] Field of Search ...................................... 558/270, 275, 558/277

[56] References Cited

U.S. PATENT DOCUMENTS

| | | | |
|---|---|---|---|
| 2,409,712 | 10/1946 | Schweitzer | 560/345 |
| 2,729,677 | 1/1956 | Gilbert et al. | 564/53 |
| 3,114,762 | 12/1963 | Mador et al. | 558/270 |
| 4,062,884 | 12/1977 | Romano et al. | 558/277 |
| 4,218,391 | 8/1980 | Romano et al. | 558/277 |
| 4,229,589 | 10/1980 | Nishimura et al. | 558/277 |
| 4,229,591 | 10/1980 | Nishimura et al. | 558/277 |
| 4,327,035 | 4/1982 | Heitz et al. | 558/275 |
| 4,434,105 | 2/1984 | Buysch et al. | 558/277 |

*Primary Examiner*—Gary Geist
*Assistant Examiner*—Dwayne C. Jones
*Attorney, Agent, or Firm*—Lowe, Price, LeBlanc & Becker

[57] ABSTRACT

A process for preparing carbonate compounds having the following formula:

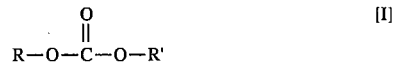

$$R-O-\overset{\overset{\displaystyle O}{\|}}{C}-O-R' \qquad [I]$$

wherein R and R' are, the same or different, $C_1$–$C_6$ alkyl group, a $C_3$–$C_6$ cycloalkyl group, an optionally substituted $C_6$–$C_{14}$ aryl group, an alkylaryl group, or an arylalkyl group is proposed; the process comprises reacting urea or derivatives thereof with appropriate alcohols or phenols and preparing the carbonate compounds via a multiple-step synthesis process.

12 Claims, No Drawings

PROCESS FOR PREPARING CARBONATE COMPOUNDS

BACKGROUND OF THE INVENTION

1. Field of the Invention

The present invention relates to a process for preparing carbonate compounds via a multiple-step synthesis process.

2. Description of Prior Art

Conventionally, a phosgene process and a non-phosgene process are used for producing carbonate compounds. In the phosgene process, phosgene is reacted with alcohols in the absence of catalyst at a low temperature to produce carbonate compounds; the phosgene process, however, has problems such as highly toxic phosgene is used as a starting compound, and a special manufacturing facility required to cope with the highly corrosive by-product (hydrochloric acid) generated by the process; such facility is very costly. Furthermore, extremely high amount of chlorine is often contained in the resulting carbonate products.

The non-phosgene process can be roughly divided into alcohols/carbon monooxide oxidation process, alkyl nitrite process and transesterification process. These processes will be described in detail as follows:

The alcohols/carbon monooxide oxidation process can be further divided into a liquid phase process and a gas phase process; for the liquid phase process as described in the U.S. Pat. No. 4,218,391, a high reaction pressure and a corrosive catalyst are required; therefore, special facilities are in need and such facilities are very costly for the process. In addition, the resulting carbonate products always contain a large amount of water and a great deal of energy is wasted in purification process for removing the water from the carbonate products. The gas phase process as described in the U.S. Pat. No. 3,114,762 avoids the need of high reaction pressure in the liquid phase process; however, because heterogeneous catalyst is used the yield of product is low, and the catalyst used in the process is toxic.

The alkyl nitrite process also includes a liquid phase process and a gas phase process. The liquid phase process as described in the U.S. Pat. No. 4,229,589 relates to the reaction of carbon monooxide with alkyl nitrite in the presence of metallic palladium as catalyst under a high pressure to obtain carbonate compounds. Nevertheless, there are problems in this process such that the yield is low and a costly facility is needed. The gas phase process as described in the U.S. Pat. No. 4,229,591 employs the catalytic reaction of carbon monooxide with alkyl nitrite, which reaction is carried out under a low pressure and gas phase. The disadvantage with the above process is that the cost for recycling the alkyl nitrite from the resulting products is high.

The transesterification process can be further divided into the following two processes according to the starting materials used: one is the process (see U.S. Pat. No. 4,434,105) which involves the catalytic reaction of alcohols, ethylene oxide and carbon dioxide in liquid phase; and another one is the process (see U.S. Pat. No. 4,062,884) which involves the catalytic reaction of alcohols and ethylene carbonate in liquid phase. The disadvantages of these processes are such that the cost of the preparation of ethylene oxide or ethylene carbonate, to be used as the starting material, is high and, in order to obtain a high selectivity, the use of a large amount of alcohols is required with a high reflux ratio as a result the operating cost increases.

Under the circumstances mentioned above, attempts had been made in order to overcome the disadvantages described above through the inventors' extensive and intensive studies, and the present invention was thus completed.

SUMMARY OF THE INVENTION

It is the main object of the present invention to provide an improved process for preparing alkyl carbonates, which comprises reacting urea or derivatives thereof with appropriate alcohols or phenols to produce carbonate compounds via a multiple step synthesis process. While compared with the conventional processes for preparing alkyl carbonates, the process of the present invention provides the following advantages:

1. By using the urea derivatives as starting material, the cost of raw material is reduced;
2. The use of noble metal as catalyst is optional such that the cost of catalyst is reduced when non-noble metal is employed as catalyst;
3. Homogeneous catalysts are used in this invention which results in a high selectivity for the reaction; the catalysts are not corrosive, and can be recovered for re-use;
4. The reaction is carried out under low pressure and liquid phase, therefore, problems existing in a high pressure reaction such as high degree of danger and high cost in facility as well as in operation are eliminated; and
5. No water is produced throughout the process reactions of the present invention, so the catalyst will be free from being poisoned by the combination of water and the catalyst, and side reactions which adversely affect the cost of the purification of the resulting alkyl carbonates can be avoided.

DETAILED DESCRIPTION OF THE INVENTION

The present invention is directed to a process for preparing carbonate compounds represented by the following formula [I]:

wherein R and R' are, the same or different, a $C_1$–$C_6$ alkyl group, a $C_3$–$C_6$ cycloalkyl group, an optionally substituted $C_6$–$C_{14}$ aryl group, an alkylaryl group, or an arylalkyl group; the carbonate compounds can be prepared according to the following reaction scheme A:

Reaction Scheme A:

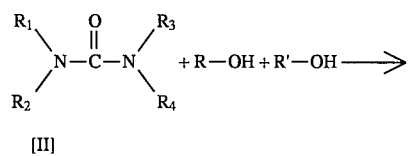

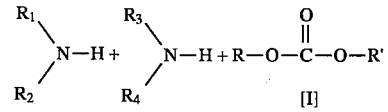

wherein R and R' are defined as above, and $R_1$, $R_2$, $R_3$ and $R_4$ are, the same or different, hydrogen, a $C_1$–$C_6$ alkyl group, a $C_3$–$C_6$ cycloalkyl group, an option-ally substituted $C_6$–$C_{14}$ aryl group, an alkylaryl group, or an arylalkyl group; or $R_1$ and $R_2$, or $R_3$ and $R_4$ may be bonded together with the nitrogen atom adjacent thereto to form an optionally substituted nitrogen-containing five- or six- member heterocyclic ring. The term "$C_1$–$C_6$ alkyl group" described herein includes a straight- or branched- alkyl group, such as methyl, ethyl, n-propyl, isopropyl, n-butyl, s-butyl, butyl, n-pentyl, neo-pentyl, isopentyl and n-hexyl.

Examples of the "$C_3$–$C_6$ cycloalkyl group" include cyclopropyl, cyclobutyl, cyclopentyl, cyclohexyl, and the like.

Examples of the "$C_6$–$C_{14}$ aryl group" include phenyl, naphthyl and anthryl, and the like.

Examples of the "arylalkyl group" include phenylmethyl, phenylethyl, phenyl propyl, and the like.

Examples of the "alkylaryl group" include methylphenyl, ethylphenyl, and the like.

Examples of the "nitrogen-containing heterocyclic ring", which can be formed by the linking of $R_1$ and $R_2$, or $R_3$ and $R_4$ with the nitrogen atom adjacent thereto, include pyrrolidyl, pyrazolidinyl, imidazolidinyl, piperidinyl, piperazinyl, and the like.

Examples of the substituents for the aryl, arylalkyl, alkylaryl, and the nitrogen-containing heterocyclic ring include hydroxyl, $C_1$–$C_4$ alkyl, $C_1$–$C_4$ alkoxyl, hydroxyl-($C_1$–$C_4$)alkyl, amino, $C_1$–$C_4$ alkoxylcarbonyl, N-monosubstituted amino, N,N-disubstituted amino, nitro, halogen, $C_1$–$C_4$ alkylthio, thiol groups, and the like.

The starting material [II] in the reaction scheme A can be the compounds exemplified as follows:

The process of the present invention according to reaction scheme A is composed of reactions represented by the following reaction schemes A1, A2 and A3. These reactions will be described in detail, accompanied with the following reaction schemes, as follows:

Reaction Scheme A1

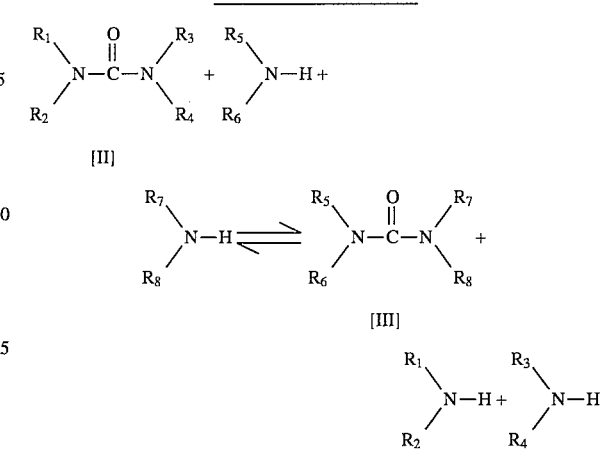

wherein $R_1$, $R_2$, $R_3$ and $R_4$ are defined as above; and $R_5$, $R_6$, $R_7$ and $R_8$ are, the same or different, hydrogen, a $C_1$–$C_6$ alkyl group, a $C_1$–$C_6$ alkoxyl group, a $C_1$–$C_6$ alkoxycarbonyl group, a substituted or unsubstituted phenyl group, provided that at least one of $R_5$ and $R_6$ is a substituted or unsubstituted phenyl group, and that at least one of $R_7$ and $R_8$ is a substituted or unsubstituted phenyl group Examples of the substituents on the substituted phenyl group are a $C_1$–$C_6$ alkyl group, a nitro group, an amino group, a halogen, a hydroxyl group, a $C_1$–$C_4$ alkoxyl group, a $C_1$–$C_4$ alkylthio group, a thiol group, and the like; the number of the substituents is from 1 to 4, preferably 1 to 2.

The reaction according to the reaction scheme A1 is carried out in the presence or absence of catalyst under atmospheric pressure at a temperature from 100° to 300° C.,

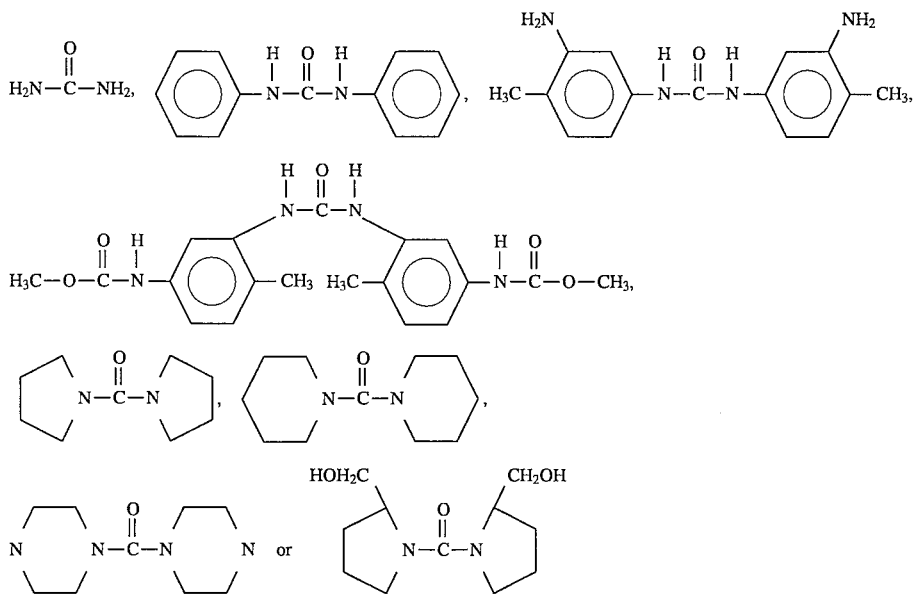

preferably 120° to 180° C., for a period from 1 to 4 hours (see U.S. Pat. No. 2,729,677).

According to the following reaction scheme A2, the resulting product [III] from the reaction of scheme A1 is further reacted with alcohols or phenols.

Reactions Scheme A2

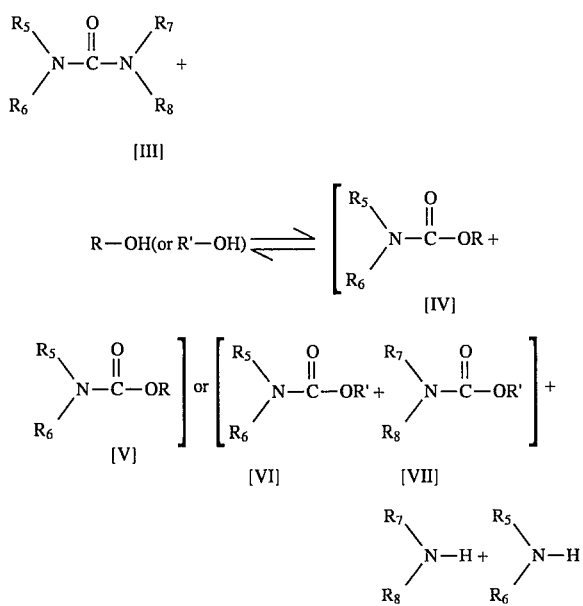

wherein the symbols have the same meaning as above.

The reaction according to reaction scheme A2 is carried out in the presence or absence of catalyst at a temperature from 100° to 300° C., preferably from 140° to 200° C., in a pressurized reactor whose pressure is self-provided (see U.S. Pat. 2,409,712)

According to the following reaction scheme A3, the resulting products [IV] to [VII] from the reaction of scheme A2 may be further subject to either independently versatile decomposition or replacement reaction between products [IV] and [V] or products [VI] and [VII] to give the compounds represented by formula [I]. The reaction scheme is shown as follows:

The reaction according to reaction scheme A3 is carried out in the presence of catalyst at a temperature from 100° to 300° C., preferably 140° to 200° C., under atmospheric pressure, reduced pressure or pressurized condition.

The amount of catalyst used is in the range between 0.001 and 10% by weight, preferably between 0.01 and 5% by weight based on the total weight of reactants.

The catalyst used in the present invention, which can be used alone or in combination with others, is selected from the group consisting of the following compounds (A) through (H):

(A) hydroxides, oxides, hydrides, alcoholates and halides of alkali metal or alkali earth metal, and alkali metal or alkali earth metal salts of organic and inorganic acid, such as LiOH, NaOH, KOH, Mg(OH)$_2$, Ca(OH)$_2$; Li$_2$CO$_3$, Na$_2$CO$_3$, Na$_2$CO$_3$, K$_2$CO$_3$MgCO$_3$, CaCO$_3$, BaCO$_3$; LiBH$_4$, NaBH$_4$, KBH$_4$, Mg(BH$_4$)$_2$, Ca(BH$_4$)$_2$; Li$_2$HPO$_4$, Na$_2$HPO$_4$, K$_2$HPO$_4$, MgHPO$_4$, CaHPO$_4$; LiCl, NaCl, KCl, MgCl$_2$, CaCl$_2$; Li(CH$_3$COO), Na(CH$_3$COO), K(CH$_3$COO), Mg(CH$_3$COO)$_2$, Ca(CH$_3$COO)$_2$, lithium, sodium or potassium phenolate, and lithium, sodium or potassium bisphenol A;

(B) titanium- and zirconium-containing compounds such as TiCl$_4$, Ti(OR)$_4$, ZrCl$_4$, Zr(OR)$_4$, etc.;

(C) iron-, cobalt- and nickel-containing compounds, especially the complexes thereof, etc.;

(D) zinc-, cadmium-, gallium-, tin-, lead-, antimony- and bismuth-containing compounds, preferably zinc-, tin-, lead- and antimony-containing complexes and oxides, such as R$_2$SnO wherein R is alkyl, aryl, arylalkyl or alkylaryl group, or Sb$_2$O$_3$, etc.

(E) borates such as B(OR)$_n$(OH)$_{3-n}$ wherein n is 1, 2 or 3, for example, B(OMe)$_3$, B(OMe)$_2$OH; B(OMe)(OH)$_2$, B(OPh)$_3$, etc.

(F) amino compounds including primary, secondary, tertiary amine and quaternary ammonium salt, for example, RNH$_2$, R$_2$NH, R$_3$N and R$_4$N$^+$X$^-$ wherein R is alkyl, aryl, arylalkyl or alkylaryl group, such as Reactions Scheme A3

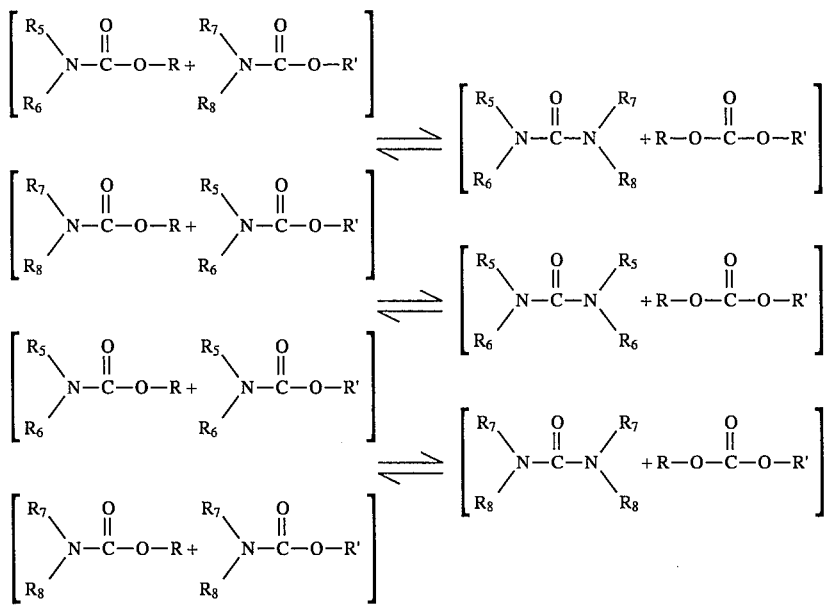

$(CH_3)_4N^+Cl^-$, $(CH_3)_4N^+Br^-$, $(CH_3)_4N^+OH^-$, etc. electron-donating nitrogen-containing heterocyclic compounds:
  (a) pyridines such as 4-aminopyridine, 2-aminopyridine, 4-dimethylaminopyridine, 4-hydroxypyridine, 2-hydroxypyridine, 4-methoxypyridine, and 4-mercapto-pyridine;
  (b) imidazoles such as imidazole, 2-methylimidazole, 4-methylimidazole, 2-dimethylaminoimidazole, 2-methoxyimidazole, and 2-thioimidazole.
  (c) others such as picoline, pyrimidine, pyrazole, aminoquinoline, pyrrolidine, morpholine, piperidine, piperazine, and pyrrole.

(H) electron-donating phosphorus-containing compounds, for example, phosphines and phosphites, such as trimethyl phosphine, triphenyl phosphine, trimethyl phosphite, triphenyl phosphite and tris(tolyl) phosphite.

The process according to this invention will now be described in detail with reference to the following examples; however, the invention is not limited thereto.

EXAMPLE 1

To at three-liter reactor were added 180 grams of urea and 2,232 grams of aniline. The mixture was heated to 160° C. and subjected to reaction for 4 hours under stirring. The mixture was then cooled to a temperature below 20° C. and sampled for the analysis of HPLC. The product N,N'-diphenylurea (abbreviated as DPU; chemical formula:

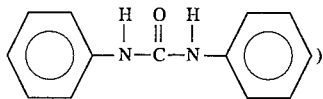

was obtained at a yield of 99.5%

EXAMPLE 2

To a two-liter reactor were added 424 grams of DPU obtained from Example 1 and 800 grams of methanol. The mixture was heated to 160° C. and subjected to reaction for 3 hours under stirring. The mixture was then cooled to, a temperature below 20° C. and sampled for the analysis of HPLC. A conversion of 99.6% for DPU and a selectivity of 99.4% for the resulting product methyl N-phenylcarbamate (abbreviated as MNPC; chemical formula:

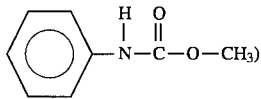

were found.

EXAMPLE 3

To a two-liter reactor were added 424 grams of DPU obtained from Example 1 and 1,150 grams of ethanol. The mixture was heated to 170° C. and subjected to reaction for 3 hours under stirring. The mixture was then cooled to a temperature below 20° C. and sampled for the analysis of HPLC. A conversion of 98.4% for DPU and a selectivity of 99.0% for the resulting product ethyl N-phenylcarbamate (abbreviated as ENPC; chemical formula:

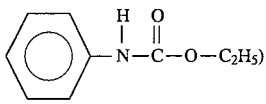

were found.

EXAMPLE 4

To a two-liter reactor were added 318 grams of DPU obtained from Example 1 and 1,388 grams of n-butylalcohol. The mixture was heated to 180° C. and subjected to reaction for 3 hours under stirring. The mixture was then cooled to a temperature below 20° C. and sampled for the analysis of HPLC. A conversion of resulting 96.2% for DPU., and a selectivity of 98.1% for the resulting product n-butyl N-phenylcarbamate (abbreviated as BNPC; chemical formula:

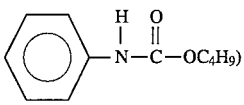

were found.

EXAMPLE 5

To two-liter reactor were added 318 grams of DPU obtained from Example 1 and 2,350 grams of phenol. The mixture was heated to 180° C. and subjected to reaction for 4 hours under stirring. The mixture was then cooled to a temperature below 20° C. and sampled for the analysis of HPLC. A conversion of 91.2% for DPU and a selectivity of 88% for the resulting product phenyl N-phenylcarbamate (abbreviated as PNPC; chemical formula:

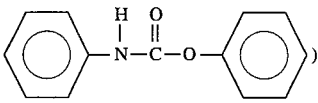

were found.

EXAMPLE 6

To a one-liter reactor were added 500 grams of MNPC obtained from Example 2 and 5 grams of $Pb(OAC)_2.3H_2O$. The mixture was heated to 180° C. and subjected to reaction for 3.5 hours with stirring. After the reaction was completed, the mixture was cooled to a temperature below 20° C. and sampled for the analysis of HPLC and GC. A conversion of 87.3% for MNPC and a selectivity of 85.2% for the resulting product dimethyl carbonate (abbreviated as DMC; chemical formula: $H_3C-O-CO-O-CH_3$) were found.

EXAMPLE 7

To a one-liter reactor were added 500 grams of MNPC obtained from Example 2 and 10 grams of $Mg(OAC)_2.2H_2O$. The mixture was heated to 170° C. and subjected to reaction for 4 hours under stirring.

After the reaction was completed, the mixture was cooled to a temperature below 20° C. and sampled for the analysis of HPLC and GC. A conversion of 75.4% for MNPC and a selectivity of 77.6% for DMC were found.

EXAMPLE 8

To a one-liter reactor were added 500 grams of MNPC obtained from Example 2 and 1 gram of KI. The mixture was heated to 160° C. and subjected to reaction for 6 hours under stirring.

After the reaction was completed, the mixture was cooled to a temperature below 20° C. and sampled for the analysis of HPLC and GC. A conversion of 81.8% for MNPC and a selectivity of 80.1% for DMC were found.

EXAMPLE 9

To a one-liter reactor were added 500 grams ENPC obtained from Example 3 and 5 grams of $Ti(OPr)_4$. The mixture was heated to 180° C. and subjected to reaction for 5 hours under stirring.

After the reaction was completed, the mixture was cooled to a temperature below 20° C. and sampled for the analysis of HPLC and GC. A conversion of 75.0% for ENPC and a selectivity of 69.7% for the resulting product diethyl carbonate (abbreviated as DEC; chemical formula: $H_5C_2$—O—CO—$C_2H_5$) were found.

EXAMPLE 10

To a one liter reactor were added 500 grams of ENPC obtained form Example 3 and 10 grams of $Na_2CO_3$. The mixture was heated to 180° C. and subjected to reaction for 6 hours under stirring.

After the reaction was completed, the mixture was cooled to a temperature below 20° C. and sampled for the analysis of HPLC and GC. A conversion of 68.2% for ENPC and a selectivity of 53.2% for DEC were found.

EXAMPLE 11

To a one-liter reactor were added 500 grams of BNPC obtained from Example 4 and 1 gram of N,N-dimethyltolylamine. The mixture was heated to 160° C. and subjected to reaction for 6 hours under stirring.

After the reaction was completed, the mixture was cooled to a temperature below 20° C. and sampled for the analysis of HPLC and GC. A conversion of 60.1% for BNPC and a selectivity of 45.5% for the resulting product di-n-butyl carbonate (abbreviated as DBC; chemical formula: $H_9C_4$—O—CO—O—$C_4H_9$) were found.

EXAMPLE 12

To a one, liter reactor were added 500 grams of BNPC obtained from Example 4 and, 1 gram of $Pb(OAC)_2 \cdot 3H_2O$ and 1 gram of $NaOCH_3$. The mixture was heated to 160° C. and subjected to reaction for 6 hours under stirring.

After the reaction was completed, the mixture was cooled to a temperature below 20° C. and sampled for the analysis of HPLC and GC. A conversion of 82.5% for BNPC and a selectivity of 76.7% for DBC were found.

EXAMPLE 13

To a one-liter, reactor were added 250 grams of MNPC obtained from example 2 and 250 grams of ENPC obtained from Example 3 and 1 gram of $Zr(NO_3)_4$. The mixture was heated to 180° C. and subjected to reaction for 5 hours under stirring.

After the reaction was completed, the mixture was cooled to a temperature below 20° C. and sampled for the analysis of HPLC and GC. A conversion of 80.4% for (MNPC+ENPC) and selectivities of 26.1%, 8.8% and 36.5% for DMC, DEC and the resulting product ethyl methyl carbonate (abbreviated as EMC; chemical formula: $H_5C_2$—O—CO—O—$CH_3$), respectively, were found.

EXAMPLE 14

To a one-liter reactor were added 500 grams of PNPC obtained from Example 5 and 3 grams of LiCl. The mixture was heated to 180° C. and subjected to reaction for 6 hours under stirring.

After the reaction was completed, the mixture was cooled to a temperature below 20° C. and sampled for the analysis of HPLC and GC. A conversion of 75.2% for PNPC and a selectivity of 36.4% for the resulting product diphenyl carbonate (abbreviated as DPC; chemical formula:

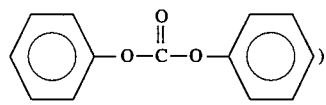

were found.

We claim:

1. A process for preparing carbonates represented by formula $$R-O-\underset{\underset{O}{\|}}{C}-O-R' \qquad [I]$$

wherein R and R' may be the same or different, and are a $C_1$–$C_6$ alkyl group, a $C_3$–$C_6$ cycloalkyl group, an optionally substituted $C_6$–$C_{14}$ aryl group, an alkylaryl group or an arylalkyl group; said process comprising the steps of:

(1) reacting a urea derivative represented by formula

wherein $R_1$, $R_2$, $R_3$ and $R_4$ may be the same or different, and are hydrogen, a $C_1$–$C_6$ alkyl group, a $C_3$–$C_6$ cycloalkyl group, an optionally substituted $C_6$–$C_{14}$ aryl group, an alkylaryl group or an arylalkyl group; or $R_1$ and $R_2$, or $R_3$ and $R_4$ are bonded together with a nitrogen atom adjacent thereto to form an optionally substituted nitrogen-containing five- or six- member heterocyclic ring, with compounds represented by formula and for 1 to 4 hours:

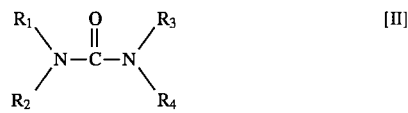

wherein $R_5$, $R_6$, $R_7$ and $R_8$ may be the same or different, and are hydrogen, a $C_1$–$C_6$ alkyl group, a $C_1$–$C_6$ alkoxyl group, a $C_1$–$C_6$ alkoxy carbonyl group, a substituted or unsubstituted phenyl group; provided that at least one of $R_5$ and $R_6$ is a substituted or unsubstituted phenyl group, and at least one of $R_7$ and $R_8$ is a substituted or unsubstituted phenyl group, to give compounds represented by formula:

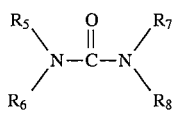 [III]

wherein $R_5$, $R_6$, $R_7$ and $R_8$ are defined as above;

(2) reacting the resulting compound represented by formula with R—OH and/or R'—OH, wherein R and R' are defined as above, to give compounds represented by formulas to:

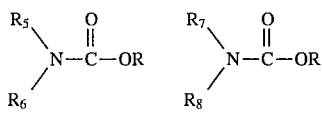

[IV]　　　　[V]

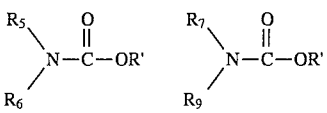

[VI]　　　　[VII]

(3) recovering and then allowing the compounds represented by formulas to either independently versatilely decompose or to carry out replacement compounds and or compounds and between them in the presence of not more than one catalyst to obtain the carbonate compounds represented by formula wherein reaction steps (1) to (3) are performed at a temperature below about 200° C.

2. The process of claim 1, wherein the substituents on the substituted phenyl group for $R_5$ to $R_8$ are selected from the group consisting of $C_1$–$C_6$ alkyl, nitro, amino, halogen, hydroxy, $C_1$–$C_4$ alkoxyl, $C_1$–$C_4$ alkylthio and thiol group.

3. The process of claim 1, wherein the substituents on the substituted aryl, alkylaryl, arylalkyl and nitrogen-containing five- or six- member heterocyclic group for R, R', and $R_1$ to $R_4$ are selected from the group consisting of hydroxy, $C_1$–$C_4$ alkyl, $C_1$–$C_4$ alkoxy, hydroxy-($C_1$–$C_4$) alkyl, amino, $C_1$–$C_4$ alkoxycarbonyl, N-monosubstituted amino, N,N-disubstituted amino, nitro, halogen, $C_1$–$C_4$ alkylthio and thiol group.

4. The process of claim 1, wherein the optionally substituted five- or six- member heterocyclic group which is formed by bonding $R_1$ and $R_2$ or $R_3$ and $R_4$ together with the nitrogen atom adjacent thereto is selected from the group consisting of pyrrolidyl, pyrazolidinyl, imidazolidinyl, piperidinyl and piperazinyl.

5. The process of claim 1, wherein the catalyst used in step (3) is selected from the group consisting of:

(a) hydroxides, oxides, hydrides, alcoholates and halides of alkali metal or alkali earth metal, and alkali metal or alkali earth metal salts of organic and inorganic acid;

(b) titanium - and zirconium - containing compounds;

(c) iron-, cobalt-, and nickel-containing compounds;

(d) zinc-, tin-, lead- and antimony-containing complexes and oxides;

(e) borates represented by $B(OR)_n(OH)_{3-n}$, wherein n is 1, 2 or 3 and wherein R is lower alkyl or a substituted or unsubstituted phenyl group;

(f) basic amino compounds including quaternary ammonium salt, tertiary amine, secondary amine and primary amine;

(g) electron-donating nitrogen-containing heterocyclic compounds including pyridines, imidazoles, picoline, pyrimidine, pyrazole, aminoquinoline, pyrrolidine, morpholine, piperidine, piperazine and pyrrole; and (h) electron-donating phosphorus-containing compounds including phosphines and phosphites.

6. The process of claim 1, wherein the process is for preparing carbonates represented by the formula

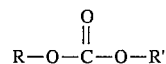

wherein R and R' may be the same or different and are a $C_1$–$C_6$ alkyl group or a $C_3$–$C_6$ cycloalkyl group.

7. A process for preparing carbonates represented by formula

 [I]

wherein R and R' may be the same or different, and are a $C_1$–$C_6$ alkyl group, a $C_3$–$C_6$ cycloalkyl group, an optionally substituted $C_6$–$C_{14}$ aryl group, an alkylaryl group or an arylalkyl group; said process comprising the steps of:

(1) reacting a urea derivative represented by formula:

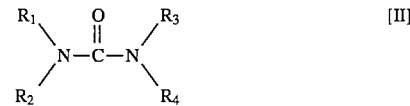 [II]

wherein $R_1$, $R_2$, $R_3$ and $R_4$ may be the same or different, and are hydrogen, a $C_1$–$C_6$ alkyl group, a $C_3$–$C_6$ cycloalkyl group, an optionally substituted $C_6$–$C_{14}$ aryl group, an alkylaryl group or an arylalkyl group; or $R_1$ and $R_2$, or $R_3$ and $R_4$ are bonded together with a nitrogen atom adjacent thereto to form an optionally substituted nitrogen-containing five- or six- member heterocyclic ring, with compounds represented by formula and for 1 to 4 hours:

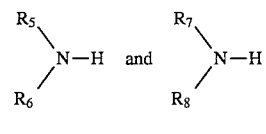

[VIII]　　　　[IX]

wherein $R_5$, $R_6$, $R_7$ and $R_8$ may be the same or different, and are hydrogen, a $C_1$–$C_6$ alkyl group, a $C_1$–$C_6$ alkoxyl group, a $C_{1-6}$ alkoxy carbonyl group, a substituted or unsubstituted phenyl group; provided that at least one of $R_5$ and $R_6$ is a substituted or unsubstituted phenyl group, and at least one of $R_7$ and $R_8$ is a substituted or unsubstituted phenyl group, to give compounds represented by formula:

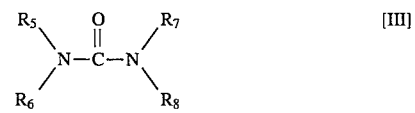 [III]

wherein $R_5$, $R_6$, $R_7$ and $R_8$ are defined as above;

(2) reacting the resulting compound represented by formula with R—OH and/or R'—OH, wherein R and R' are defined as above, to give compounds represented by formulas to:

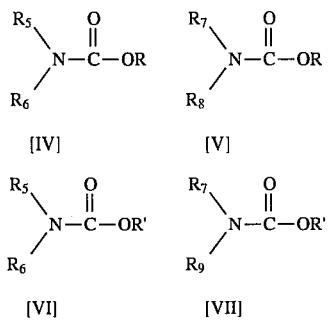

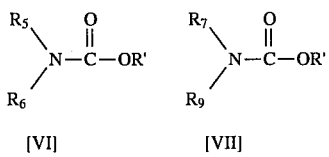

(3) recovering and then allowing the compounds represented by formulas to either independently versatilely decompose or to carry out replacement compounds and or compounds and between them in the presence of a catalyst to obtain the carbonate compounds represented by formula wherein reaction steps (1) to (3) are performed at a temperature below about 200° C.

8. The process of claim 7, wherein the catalyst used in step (3) is one or more compounds selected from the group consisting of:

(a) hydroxides, oxides, hydrides, alcoholates and halides of alkali metal or alkali earth metal, and alkali metal or alkali earth metal salts of organic and inorganic acid;

(b) titanium - and zirconium - containing compounds;

(c) iron-, cobalt-, and nickel-containing compounds;

(d) zinc-, tin-, lead- and antimony containing complexes and oxides;

(e) borates represented by $B(OR)_n(OH)_{3-n}$, wherein n is 1, 2 or 3 and wherein R is lower alkyl or a substituted or unsubstituted phenyl group;

(f) basic amino compounds including quaternary ammonium salt, tertiary amine, secondary amine and primary amine;

(g) electron-donating nitrogen-containing heterocyclic compounds including pyridines, imidazoles, picoline, pyrimidine, pyrazole, aminoquinoline, pyrrolidine, morpholine, piperidine, piperazine and pyrrole; end (h) electron-donating phosphorus-containing compounds including phosphines and phosphites.

9. The process of claim 7, wherein the process is for preparing carbonates represented by the formula

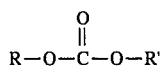

wherein R and R' may be the same or different and are a $C_1$–$C_6$ alkyl group or a $C_3$–$C_6$ cycloalkyl group.

10. A process for preparing carbonates represented by formula

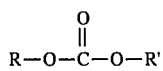  [I]

wherein R and R' may be the same or different, and are a $C_1$–$C_6$ alkyl group, a $C_3$–$C_6$ cycloalkyl group, an optionally substituted $C_6$–$C_{14}$ aryl group, an alkylaryl group or an arylalkyl group; said process comprising the step of:

recovering and allowing the compounds represented by formulas through

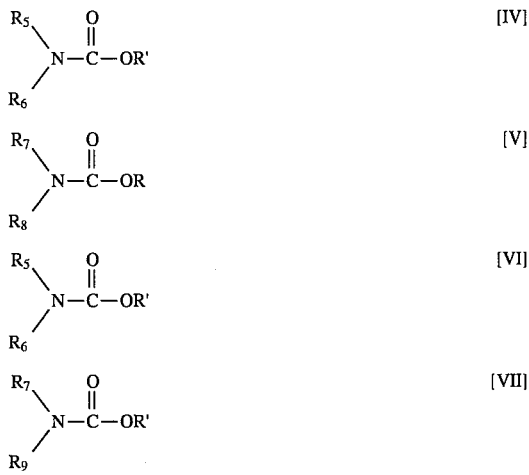

wherein $R_5$, $R_6$, $R_7$ and $R_8$ may be the same or different, and are hydrogen, a $C_1$–$C_6$ alkyl group, a $C_1$–$C_6$ alkoxyl group, a $C_1$–$C_6$ alkoxy carbonyl group, a substituted or unsubstituted phenyl group; provided that at least one of $R_5$ and $R_6$ is a substituted or unsubstituted phenyl group, and at least one of $R_7$ and $R_8$ is a substituted or unsubstituted phenyl group to either independently versatilely decompose or to carry out replacement compounds and or compounds and between them in the presence of a catalyst to obtain the carbonate compounds represented by formula wherein reaction temperature is below about 200° C.

11. The process of claim 10, wherein the catalyst used in the reaction is one or more compounds selected from the group consisting of:

(a) hydroxides, oxides, hydrides, alcoholates and halides of alkali metal or alkali earth metal, and alkali metal or alkali earth metal salts of organic and inorganic acid;

(b) titanium- and zirconium-containing compounds;

(c) iron-, cobalt-, and nickel-containing compounds;

(d) zinc-, tin-, lead- and antimony-containing complexes and oxides;

(e) borates represented by $B(OR)_n(OH)_{3-n}$, wherein n is 1, 2 or 3 and wherein R is lower alkyl or a substituted or unsubstituted phenyl group;

(f) basic amino compounds including quaternary ammonium salt, tertiary amine, secondary amine and primary amine;

(g) electron-donating nitrogen-containing heterocyclic compounds including pyridines, imidazoles, picoline, pyrimidine, pyrazole, aminoquinoline, pyrrolidine, morpholine, piperidine, piperazine and pyrrole; and (h) electron-donating phosphorus-containing compounds including phosphines and phosphites.

12. The process of claim 10, wherein the process is for preparing carbonates represented by the formula

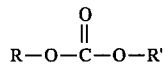

wherein R and R' may be the same or different and are a $C_1$–$C_6$ alkyl group or a $C_3$–$C_6$ cycloalkyl group.

* * * * *